United States Patent [19]

Atherton et al.

[11] 4,016,148

[45] Apr. 5, 1977

[54] PEPTIDE DERIVATIVES OF PHOSPHONIC AND PHOSPHINIC ACIDS AND INTERMEDIATES THEREFOR

[75] Inventors: Frank Ratcliffe Atherton, Welwyn Garden City; Michael John Hall; Cedric Herbert Hassall, both of Welwyn; Peter Stuart Ringrose, Royston; Robert Wilson Lambert, Welwyn, all of England

[73] Assignee: Hoffmann-La Roche Inc., Nutley, N.J.

[22] Filed: Jan. 19, 1976

[21] Appl. No.: 650,336

[30] Foreign Application Priority Data

Jan. 27, 1975 United Kingdom ............... 3417/75
Nov. 20, 1975 United Kingdom ............. 47787/75

[52] U.S. Cl. ..................... 260/112.5 R; 260/502.5; 424/177

[51] Int. Cl.$^2$ .................. C07C 103/52; C07F 9/30; C07F 9/38

[58] Field of Search ................. 260/502.5, 112.5 R

[56] References Cited

UNITED STATES PATENTS

| | | | |
|---|---|---|---|
| 3,893,992 | 7/1975 | DeBenneville | 260/112.5 R |
| 3,923,877 | 12/1975 | Barton | 260/502.5 |
| 3,954,860 | 5/1976 | Birum | 260/502.5 |
| 3,969,398 | 7/1976 | Hershman | 260/502.5 |

*Primary Examiner*—Dolph H. Torrence
*Attorney, Agent, or Firm*—Samuel L. Welt; George M. Gould

[57] ABSTRACT

The present disclosure relates to peptide derivatives. More particularly, the disclosure is concerned with peptide derivatives of phosphonic and phosphinic acids, a process for the manufacture thereof and pharmaceutical preparations containing same.

10 Claims, No Drawings

PEPTIDE DERIVATIVES OF PHOSPHONIC AND PHOSPHINIC ACIDS AND INTERMEDIATES THEREFOR

DESCRIPTION OF THE INVENTION

The peptide derivatives provided by the present invention are compounds of the general formula

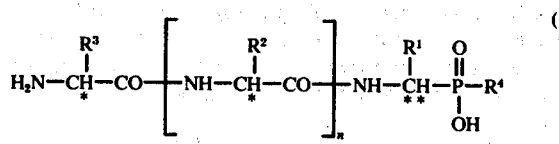

wherein $R^1$ is hydrogen, lower alkyl, lower cycloalkyl, (lower cycloalkyl)-(lower alkyl), aryl or aryl-(lower alkyl) said substituents other than hydrogen being optionally substituted by one or more of amino, hydroxy, thio, methylthio, carboxy or guanidino so as to form the characterizing group of a naturally occurring L alpha-amino acid); $R^2$ and $R^3$ each represent the characterizing group of an alpha-amino acid of the type normally found in proteins with the proviso that $R^3$ cannot be hydrogen when $n$ is zero and $R^1$ is hydrogen or phenyl; $R^4$ is hydroxy or methyl; $n$ is zero, 1, 2 or 3; the single asterisks denote that the configuration at the carbon atom so-marked is L; and the double asterisk denotes that, when $R^1$ is other than hydrogen, the configuration at the carbon atom so-marked is that which would be obtained by replacing the carboxyl group of a naturally occurring L alpha-amino acid by a phosphorus moiety [hereinafter referred to as the (R)-configuration], and their pharmaceutically acceptable salts.

As used in this specification, the term "lower alkyl" means a straight-chain or branched-chain alkyl group which preferably contains from 1 to 6 carbon atoms (e.g., methyl, ethyl, propyl, isobutyl and the like). The term "aryl" preferably comprises mono-nuclear groups such as phenyl, which may be substituted in one or more positions with hydroxy, halogen, nitro, lower alkyl or lower alkoxy substituents. The term "halogen" means fluorine, chlorine, bromine and iodine ad the term "lower alkoxy" means groups of the structure -O-(lower alkyl) wherein the lower alkyl group is as defined earlier. The expression "the characterizing group of an alpha-amino acid of the type normally found in proteins" is used to mean the residue R in a natural alpha-amino acid of the general formula

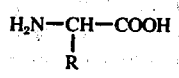

which is of the type normally occurring in proteins. Thus, for example, if the amino-acid is alanine, then the residue R represents the methyl group, in leucine the residue R represents the isobutyl group and in glutamic acid the residue R represents the 2-carboxyethyl group. R can also represent a residue which is linked with the amino nitrogen (with the loss of one of the hydrogen atoms attached thereto), thus forming a nitrogen-containing ring such as in proline and pyroglutamicacid. The term "lower cycloalkyl" means cyclic hydrocarbon groups containing 3 to 6 carbon atoms, such as cyclopropyl, cyclobutyl, cyclopentyl, cyclohexyl.

It will be appreciated that when $n$ in formula I stands for 2 or 3, the value of $R^2$ can be the same or different.

Preferred compounds of formula I hereinbefore are those wherein $R^2$ and $R^3$ each is hydrogen, methyl, isopropyl, isobutyl, benzyl, r-aminobutyl or 2-pyrrolidinyl, $R^1$ is hydrogen or methyl, $R^4$ is hydroxy and $n$ is zero or 1.

Examples of compounds of formula I hereinbefore are:
(L-alanylamino)-methylphosphonic acid,
(L-valylamino)-methylphosphonic acid,
(L-leucylamino)-methylphosphonic acid,
(L-lysylamino)-methylphosphonic acid,
(L-phenylalanylamino)-methylphosphonic acid,
(1R)-1-(L-alanylamino)-ethylphosphonic acid,
(1R)-1-glycylamino-ethylphosphonic acid,
(1R)-1-(L-alanylamino)-benzylphosphonic acid,
(1R)-1-(L-lysylamino)-ethylphosphonic acid,
(1R)-1-(L-leucylamino)-ethylphosphonic acid,
(1R-1-(L-alanylamino)-2-phenyl-ethylphosphonic acid,
(1R)-1-(L-phenylalanylamino)-ethylphosphonic acid,
(1R)-1-(L-valylamino)-ethylphosphonic acid,
(L-alanyl-L-alanylamino)-methylphosphonic acid,
(L-leucyl-L-alanylamino)-methylphosphonic acid,
(L-alanyl-L-leucylamino)-methylphosphonic acid,
(L-alanyl-L-phenylalanylamino)-methylphosphonic acid,
(L-phenylalanyl-L-phenylalanylamino)-methylphosphonic acid,
(L-phenylalanyl-L-alanylamino)-methylphosphonic acid,
(1R)-1-(L-alanyl-L-alanylamino)-ethylphosphonic acid,
(1R)-1-(glycyl-L-alanylamino)-ethylphosphonic acid,
(1R)-1-(L-valyl-L-alanylamino)-ethylphosphonic acid,
(1R)-1-(L-phenylalanyl-L-alanylamino)-ethylphosphonic acid,
(1R)-1-(L-prolyl-L-alanylamino)-ethylphosphonic acid,
(L-alanyl-L-alanyl-L-alanylamino)-methylphosphonic acid,
(1R)-1-(L-alanyl-L-alanyl-L-alanylamino)-ethylphosphonic acid,
(1R)-1-(glycyl-L-alanyl-L-alanylamino)-ethylphosphonic acid,
(1R)-1-(L-prolyl-L-alanyl-L-alanylamino)-ethylphosphonic acid,
(1R)-1-(glycyl-glycyl-L-alanylamino)-ethylphosphonic acid,
(1R)-1-(L-alanyl-L-alanyl-L-alanyl-L-alanylamino)-ethyl-phosphonic acid,
[(L-alanylamino)methyl]-methylphosphinic acid.

According to the process provided by the present invention, the peptide derivatives aforesaid (i.e., the compounds of formula I and their pharmaceutically acceptable salts) are manufactured by a. cleaving off by methods known per se the protecting group(s) present in a compound of the general formula (II)

-continued

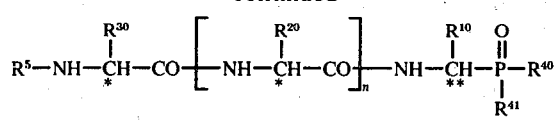

, wherein the symbols $R^{10}$, $R^{20}$ and $R^{30}$ have any of the values accorded to the symbols $R^1$, $R^2$ and $R^3$ hereinbefore respectively except that any amino group or amino groups present may be in protected form and any other functional group which may be present is in protected form where required, $R^{40}$ represents a methyl group or $R^{41}$, $R^{41}$ represents a hydroxy group or lower alkoxy protecting group, $R^5$ represents a hydrogen atom or a protecting group, and the single and double asterisks as well as $n$ have the significances given earlier, or b. separating an (R,S)-diastereomeric compound corresponding to formula I into its diastereomers and isolating the (R)-diastereomer, and, if desired, converting an obtained compound of formula I into a pharmaceutically acceptable salt.

The amino group or amino groups which may be present in $R^{10}$, $R^{20}$ and $R^{30}$ in formula II can be protected with any amino-protecting group which is well-known in peptide chemistry. Especially suitable amino-protecting groups for the purpose of the present invention are aralkoxycarbonyl groups, particularly the benzyloxycarbonyl group, and the tertbutoxycarbonyl group. The amino-protecting group may also be a formyl, trityl or trifluoroacetyl group. Any carboxy or hydroxy group which may be present in $R^{10}$, $R^{20}$ and $R^{30}$ in formula II can be protected by a conventional carboxy-protecting or hydroxy-protecting group respectively. For example, a carboxy group may be protected by conversion into an alkyl ester (e.g. a tertbutyl ester) or an aralkyl ester (e.g. a benzyl ester). Again, for example, a hydroxy group may be protected, for example, by means of an aralkoxycarbonyl group (e.g. benzyloxycarbonyl), an alkanoyl group (e.g. acetyl, propionyl etc), an aroyl group (e.g. benzoyl), a alkyl group (e.g. tertbutyl) or a aralkyl group (e.g. benzyl). The protection of other functional groups present in $R^{10}$, $R^{20}$ and $R^{30}$ may be carried out in a known manner. The protecting group denoted by $R^5$ in formula II can be any of the amino-protecting groups mentioned earlier in connection with $R^{10}$, $R^{20}$ and $R^{30}$.

The cleavage of the protecting group or protecting groups present in a compound of formula II is carried out in accordance with methods known per se; that is to say, methods in actual use for or described in the literature on the cleavage of protecting groups. Thus, for example, an aralkoxycarbonyl group (e.g. benzyloxycarbonyl) or a tertbutoxycarbonyl group may be cleaved off by hydrolysis (e.g. treatment with a mixture of hydrogen bromide and glacial acetic acid). An aralkoxycarbonyl group (e.g. benzyloxycarbonyl) can also be cleaved off by hydrolgenolysis (e.g. in the presence of palladium-on-charcoal). The tertbutoxycarbonyl group may also be cleaved off by means of hydrogen chloride in dioxan. A lower alkoxy group denoted by $R^{40}$ and/or $R^{41}$ may be converted into a hydroxy group by treatment with a mixture of hydrogen bromide in glacial acetic acid or by means of trimethylchlorosilane followed by aqueous hydrolysis. It will be appreciated that the cleavage of the protecting groups can be carried out in a single step or in more than one step depending on the nature of the protecting groups present.

The separation of an (R,S) diastereomeric compound corresponding to formula I into its diastereomers and isolation of the (R)-diastereomer can be carried out according to known methods; for example, by crystallization or by high pressure liquid chromatography and the like.

Compounds of formula I are amphoteric in nature and form pharmaceutically acceptable salts with strong acids (e.g. methanesulphonic acid, paratoluenesulphonic acid, hydrochloric acid, hydrobromic acid, sulphuric acid etc) and with bases (e.g. sodium hydroxide etc).

The starting materials of formula II hereinbefore may be prepared, for example, by condensing a compound of the general formula

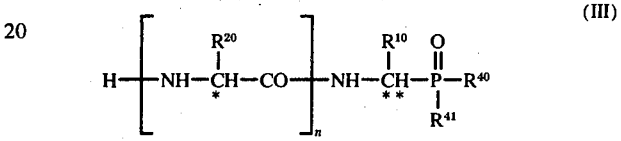

(III)

, wherein $R^{10}$, $R^{20}$, $R^{40}$, $R^{41}$, $n$ and the single and double asterisk have the significance given earlier, with an appropriately protected α-amino acid, an appropriately protected dipeptide, an appropriately protected tripeptide, an appropriately protected tetrapeptide or a reactive derivative thereof as the case may require.

Thus, when a compound of formula III in which $n$ stands for zero is used, such a compound can be condensed with an appropriately protected α-amino acid or a reactive derivative thereof to give a compound of formula II in which $n$ stands for zero, or with an appropriately protected dipeptide or a reactive derivative thereof to give a compound of formula II in which $n$ stands for 1, or with an appropriately protected tripeptide or a reactive derivative thereof to give a compound of formula II in which $n$ stands for 2 or with an appropriately protected tetrapeptide or a reactive derivative thereof to give a compound of formula II in which $n$ stands for 3.

Again, a compound of formula III in which $n$ stands for 1 can be condensed with an appropriately protected α-amino acid or a reactive derivative thereof to give a compound of formula II in which $n$ stands for 1, or with an appropriately protected dipeptide or a reactive derivative thereof to give a compound of formula II in which $n$ stands for 2 or with an appropriately protected tripeptide or a reactive derivative thereof to give a compound of formula II in which $n$ stands for 3.

Yet again, a compound of formula III in which $n$ stands for 2 can be condensed with an appropriately protected α-amino acid or a reactive derivative thereof to give a compound of formula II in which $n$ stands for 2 or with an appropriately protected dipeptide or a reactive derivative thereof to give a compound of formula II in which $n$ stands for 3.

Finally, a compound of formuala III in which $n$ stands for 3 can be condensed with an appropriately protected α-amino acid or a reactive derivative thereof to give a compound of formula II in which $n$ stands for 3.

Alternatively, the compounds of formula II can be prepared by carrying out the foregoing condensation using an (R,S) compound coresponding to formula III and separating the (R) compound from the resulting (R,S) product in a manner known per se; for example, by crystallization, chromatography or fractional crystallization using a suitable base such as α-methylbenzylamine and the like.

The aforementioned condensation can be carried out in accordance with methods which are known per se in peptide chemistry; for example, by the mixed anhydride azide, activated ester or acid chloride method.

In one method, an apropriate compound of formula III can be condensed with an apropriately protected amino acid, di-, tri- or tetrapeptide as the case may require in which the terminal carboxy function is a mixed anhydride residue formed with an organic or inorganic acid. Suitably, such an amino acid, di-, tri- or tetrapeptide carrying a free carboxy function is treated with a tertiary base such as a tri(lower alkyl)amine (e.g. triethylamine) or N-ethylmorpholine in an inert organic solvent (e.g. tetrahydrofuran, 1,2-dimethoxyethane, dichloromethane, toluene, petroleum ether or mixtures thereof) and the resulting salt is reacted with a chloroformic acid ester (e.g. the ethyl or isobutyl ester) at a low temperature. The mixed anhydride obtained is then suitably condensed in situ with the compound of formula III.

In another method, an appropriate compound of formula III can be condensed with an appropriately protected amino acid, di-, tri- or tetrapeptide as the case may require in which the terminal carboxy group is in the form of an acid azide. This condensation is preferably carried out in an inert organic solvent such as dimethylformamide or ethyl acetate at a low temperature.

In yet another method, an appropriate compound of formula III can be condensed with an appropriately protected amino acid, di-, tri- or tetrapeptide as the case may require in which the terminal carboxy function is in the form of an active ester group (e.g. the p-nitrophenyl, 2,4,5-trichlorophenyl or N-hydroxysuccinimide ester group). This condensation is suitably carried out either in an inert organic solvent such as dimethylformaide or, in the case where $R^{40}$ and/or $R^{41}$ represents a lower alkoxy group, in an aqueous alkanol (e.g. aqueous ethanol).

In a further method, an appropriate compound of formula III can be condensed with an appropriately protected amino acid, di-, tri- or tetrapeptide as the case may require in which the terminal carboxy function is in the form of an acid chloride. This condensation is preferably carried out in the presence of a base and at a low temperature.

The peptide derivatives provided by this invention potentiate the activity of antibiotics (e.g. penicillin and cephalosporin antibiotics and D-cycloserine). Thus, for example the fractional inhibitory concentration indices of (1R)-1-(L-alanylamino)-ethylphosphonic acid in combination with a cephalosporin, with a penicillin antibiotic and with D-cycloserine against E. coli in Davis minimal medium are given in Table 1.

Table 1

| Antibiotic | Minimum Inhibitory Concentration (μg/ml) | | Fractional Inhibitory Concentration Index |
|---|---|---|---|
| | Antibiotic alone | Antibiotic + peptide derivative | |
| Amoxycillin | 4 | 1 + 0.06 | 0.3 |
| D-Cycloserine | 64 | 0.25 + 0.25 | 0.25 |
| Cephradine | 16 | 4 + 0.25 | 0.5 |

Again, for example, the fractional inhibitory concentration indices of (1R)-1-(L-alanylamino)-ethylphosphonic acid (Derivative A), (1R)-1-(L-alanyl-L-alanylamino)-ethylphosphonic acid (Derivative B), (1R)-1-(L-alanyl-L-alanyl-L-alanylamino)-ethylphosphonic acid (Derivative C), (1R)-1-(L-alanyl-L-alanyl-L-alanyl-L-alanylamino)-ethylphosphonic acid (Derivative D), (1R)-1-(L-phenylalanylamino)-ethylphosphonic acid (Derivative E), (1R)-1-(L-valylamino)-ethylphosphonic acid (Derivative F) and (1R)-1-(L-leucylamino)-ethylphosphonic acid (Derivative G) in a 2:1 ratio with D-cycloserine against E. coli in Davis minimal medium are given in Table 2.

Table 2

| Peptide Derivative | Fractional Inhibitory Concentration of D-cycloserine | Fractional Inhibitory Concentration Index |
|---|---|---|
| A | 0.06 | 0.3 |
| B | 0.03 | 0.2 |
| C | 0.05 | 0.1 |
| D | 0.10 | 0.2 |
| E | 0.13 | 0.48 |
| F | 0.13 | 0.60 |
| G | 0.12 | 0.27 |

The peptide derivatives provided by this invention can be administered in combination with the antibiotic or the antibiotic and peptide derivative can be administered separately, if necessary by different routes. The ratio in which the peptide derivative and antibiotic can be administered can vary within wide limits depending on such factors as the derivative and antibiotic chosen, the route of administration and the organism to be combatted. For example, the peptide derivative and antibiotic may be administered in a ratio of from about 100:1 to 1:100.

The peptide derivatives provided by the present invention also possess an antibacterial activity against gram-positive and gram-negative organisms such as E. coli, P. vulgaris, Ps. aeuruginosa and S. aureus.

The peptide derivatives of this invention may accordingly be used as medicaments; for example, in the form of pharmaceutical preparations which contain them in association with a compatible pharmaceutical carrier material. This carrier material can be an inorganic or organic inert carrier material suitable for enteral (e.g. oral) or parenteral administration such as, for example, water, lactose, starch, magnesium stearate, gum arabic, gelatin, polyalkyleneglycols, petroleum jelly etc. The pharmaceutical preparations can be made up in a solid form (e.g. as tablets, dragees, suppositories or capsules) or in a liquid form (e.g. as solutions, suspensions or emulsions). The pharmaceutical preparations may be sterilized and may contain adjuvants such as preservatives, stabilizers, wetting agents or salts for altering the osmotic pressure.

The following Examples illustrate the present invention:

EXAMPLE 1 a. Preparation of starting material:

33.3 g (0.30 mol) of aminomethylphosphonic acid were dissolved in a mixture of 1.5 liters of water and 750 ml of ethanol. The solution was cooled to 10° C, treated portionwise with 75.6 g (0.90 mol) of solid sodium bicarbonate while stirring and then cooled to 0° C. A reagent solution of 96 g (0.30 mol) of the N-hydroxysuccinimide ester of N-benzyloxycarbonyl-L-alanine in 1 liter of hot ethanol was added dropwise rapidly during ca 10 minutes while maintaining the internal temperature below 5° C. The reagent was washed in with two 200 ml portions of ethanol. The heterogeneous mixture was stirred for a further 2 hours at 0° C and then for 24 hours at room temperature. An almost clear solution was obtained. Evaporation at room temperature followed by re-evaporation with 400 ml of water at room temperature gave a gummy solid. This solid was dissolved in 1.5 liters of water, extracted with 1.5 liters of chloroform, then with two 500 ml portions of chloroform, acidified with 2-N hydrochloric acid to give a pH value of 2 and again extracted with chloroform. Thin layer chromatography showed that the desired starting material was in the aqueous fraction. This fraction was concentrated to ca 300 ml and passed down a column of cation exchange resin (B.D.H., Zerolit 225, SRC 13, $RSO_3H$; 1.5 kg; freshly regenerated in the acid cycle). Elution with 1 liter of water followed by three 500 ml portions of water gave four acid fractions, only the first two of which contained substantial amounts [according to thin layer chromatography] of desired starting material. These two fractions were combined, evaporated and re-evaporated with water until substantially free of hydrogen chloride. There was obtained a final residue of [(N-benzyloxycarbonyl-L-alanyl)amino]-methylphosphonic acid, which was converted to the benzylamine salt as follows:

The latter residue was dissolved in 700 ml of water and titrated with 1-N benzylamine to give a pH value of 4.5; titre 240 ml; theory 300 ml. The precipitate was filtered off and crystallized from 800 ml of water. The crystals were filtered off, washed with water until the filtrate was chloride-free, then washed successively with ethanol and ether and dried. There were obtained 52 g (41% yield) of the benzylamine salt of [(N-benzyloxycarbonyl-L-alanyl)amino]-methylphosphonic acid of melting point 200°–201° C (decomposition); $[\alpha]_D^{20} = -6.7°$ (c = 1% in acetic acid). Concentration of the mother liquors gave a further crop of 4.2 g; melting point 199°–201° C (decomposition); $[\alpha]_D^{20} = -7.4°$ (c = 1% in acetic acid).

b. The process 56.2 g of the benzylamine salt of [(N-benzyloxycarbonyl-L-alanyl)amino]-methylphosphonic acid were dissolved in a minimum volume of 2-N ammonium hydroxide and passed down a column of cation exchange resin (B.D.H., Zerolit 225, SRC 13, $RSO_3H$; 1.5 kg; freshly regenerated in the acid cycle). Elution with water gave a total acid eluate of ca 3.5 liters which was concentrated to ca 600 ml. There were added 600 ml of methanol, 0.1 ml of glacial acetic acid and 7 g of a 5% palladium on charcoal catalyst. The mixture was hydrogenated at room temperature and atmospheric pressure. The catalyst was filtered off and the solvent evaporated. The residue was evaporated with three 100 ml portions of n-propanol to give 28 g of a solid of melting point ca 260° C (decomposition). This solid was crystallized from 120 ml of water and 160 ml of ethanol to give 16.6 g of (L-alanylamino)-methylphosphonic acid of melting point 276°–282° C; $[\alpha]_D^{20} = +34.3°$ (c = 1% in water). After recrystallization from water, there were obtained 14.1 g of pure product of melting point 284°–286° C (decompostion); $[\alpha]_D^{20} = +32.9°$ (c = 1% in water).

EXAMPLE 2 a. Prepartion of starting material:

24.2 g (0.24 mol) of triethylamine were added to 53.5 g (0.24 mol) of N-benzyloxycarbonyl-L-alanine in 2 liters of dry toluene and the mixture was cooled to −5° C. 32.8 g (0.24 mol) of isobutyl chloroformate were added dropwise while stirring and the mixture was maintained at −5° C for a further 25 minutes. While stirring this mixture at −5° C, there was added dropwise a solution of 6.66 g (0.060 mol) of aminomethylphosphonic acid in 60 ml of 2-N sodium hydroxide and the stirring continued for a further 3 hours at −5° C. The mixture was then allowed to warm to room temperature and stirred overnight. The aqueous layer was separated, back-extracted with toluene and adjusted to pH 9.5 with 45 ml of 2-N sodium hydroxide. The solution was evaporated at room temperature to remove triethylamine. The residue was dissolved in 200 ml of water three times and re-evaporated each time. The final residue was dissolved in 500 ml of water and the resulting solution extracted three times with 350 ml portions of chloroform. The aqueous layer was adjusted to pH 2.5 with 50 ml of 2-N hydrochloric acid and then extracted successively with three 350 ml portions of ether and three 350 ml portions of chloroform. The aqueous layer was evaporated at room temperature and the resulting white solid dissolved in 50 ml of water and 20 ml of 2-N ammonium hydroxide and then passed down a column of cation exchange resin (B.D.H., Zerolit 225, SRC 13, $RSO_3H$; 250 g; freshly regenerated in the acid cycle). The column was eluted with water and the acid eluate evaporated. The residue was evaporated at room temperature three times with 100 ml of water each time to remove hydrogen chloride. There was obtained a final residue of [(N-benzyloxycarbonyl-L-alanyl)amino]-methylphosphonic acid, which was converted to its benzylamine salt as follows:

The latter residue was titrated with 36 ml of 1-M benzylamine to pH 4. Evaporation gave a white solid which was purified by crystallization from water. There were obtained two 0.9 g crops of the benzylamine salt of [(N-benzyloxycarbonyl-L-alanyl)amino]-methylphosphonic acid with respective metling points of 193°–195° C (decomposition) and 196°–199° C (decompostion); $[\alpha]_D^{20} = -6.0°$ (c = 1% in acetic acid).

b. The process

The benzylamine salt of [(N-benzyloxycarbonyl-L-alanyl)-amino]-methylphosphonic acid prepared in the previous paragraph was converted to (L-alanylamino)-methylphosphonic acid in a manner analogous to that described in Example 1 b).

EXAMPLE 3 a. Preparation of starting material:

In a manner analogous to Example 2(a), starting from N-benzyloxycarbonyl-L-valine there was obtained the benzylamine salt of [(N-benzyloxycarbonyl-L- valyl)amino]-methylphosphonic acid of melting point 235°–237° C (decomposition); $[\alpha]_D^{20} = -5.7°$ ($c = 0.1\%$ in acetic acid).

b. The process

In a manner analogous to Example 1 b), starting from the benzylamine salt of [(N-benzyloxycarbonyl-L-valyl)amino]-methylphosphonic acid there was obtained (L-valylamino)-methyl-phosphonic acid of melting point 290°–292° C (decomposition); $[\alpha]_D^{20} = +67.9°$ ($c = 0.85\%$ in water).

EXAMPLE 4 a. Preparation of starting material

In a manner analogous to Example 1(a), starting from the N-hydroxysuccinimide ester of N-benzyloxycarbonyl-L-leucine there was obtained the benzylamine salt of [(N-benzyloxycarbonyl-L-leucyl)amino]-methylphosphonic acid of melting point 175°–178° C (decomposition); $[\alpha]_D^{20} = -10.1°$ ($c = 0.77\%$ in acetic acid).

b. The process:

In a manner analogous to Example 1(b), starting from the benzylamine salt of [(N-benzyloxycarbonyl-L-leucyl)amino]-methylphosphonic acid there was obtained (L-leucylamino)-methylphosphonic acid of melting point 262°–264° C (decomposition); $[\alpha]_D^{20} = +59.7°$ ($c = 0.67\%$ in water).

EXAMPLE 5 a. Preparation of starting material

In a manner analogous to Example 1 a), starting from the N-hydroxysuccinimide ester of $N^2$, $N^6$-bis(benzyloxycarbonyl)-L-lysine there was obtained [[$N^2$, $N^6$-bis(benzyloxycarbonyl)-L-lysyl]amino]-methylphosphonic acid of melting point 160°–162° C (decomposition); $[\alpha]_D^{20} = -9.55°$ ($c = 0.5\%$ in ethanol). This compound was employed in the next step as the free acid.

b. The process

In a manner analogous to Example 1 b), but with hydrogenation in the presence of 2-N hydrochloric acid, starting from [[$N^2$,$N^6$-bis(benzyloxycarbonyl)-L-lysyl]amino]-methylphosphonic acid there was obtained (L-lysylamino)-methylphosphonic acid dihydrochloride of melting point 212°–217° C (decomposition); $[\alpha]_D^{20} = +22.35°$ ($c = 1\%$ in water).

EXAMPLE 6 a. Preparation of starting material

In a manner analogous to Example 1(a), but with the ion exchange carried out in methanol/water instead of water, starting from the N-hydroxysuccinimide ester of N-benzyloxycarbonyl-L-phenylalanine there was obtained [(N-benzyloxycarbonyl-L-phenylalanyl)amino]-methylphosphonic acid of melting point 181°–182° C (decomposition); $[\alpha]_D^{20} = -11.9°$ ($c = 1.0\%$ in methanol). This compound was used in the next step as the free acid.

b. The process

In a manner analogous to Example 1(b), starting from [(N-benzyloxycarbonyl-L-phenylalanyl)amino]-methylphosphonic acid there was obtained (L-phenylalanylamino)-methylphosphonic acid of melting point 252°–255° C (decomposition); $[\alpha]_D^{20} = +67.8°$ ($c = 0.51\%$ in water).

EXAMPLE 7 a. Preparation of the starting material 0.91 g (0.005 mol) of (L-alanylamino)-methylphosphonic acid were dissolved in 25 ml of water and 12.5 ml of ethanol and treated with 1.26 g (0.015 mol) of solid sodium bicarbonate to give a clear solution. The solution was stirred at 0° C while a warm solution of 1.6 g (0.005 mol) of the N-hydroxysuccinimide ester of N-benzyloxycarbonyl-L-alanine in 16 ml of ethanol was added and then washed in with two 5 ml portions of ethanol. The initially heterogeneous mixture became homogeneous within 5 minutes. The mixture was stirred at 0° C for 2 hours and then at room temperature for 16 hours. The ethanol was evaporated and the residue re-evaporated with water. The residue was dissolved in 100 ml of water and extracted with 100 ml of chloroform followed by two 50 ml portions of chloroform. The aqueous layer was acidified with ca 15 ml of 2-N hydrochloric acid to pH 2 and extracted with 100 ml of chloroform and then two 50 ml portions of chloroform. Thin layer chromatography showed that the product was in the aqueous phase. The aqueous phase was concentrated until a solid began to precipitate. The minimum amount of 2-N ammonium hydroxide to give a clear solution was added. The solution was passed down a column of cation exchange resin (B.D.H., Zerolit 225, SRC 13, $RSO_3H$; 150 g; freshly regenerated in the acid cycle) and eluted with water. The acid eluates which contained only the desired starting material (according to thin layer chromatography, three 100 ml portions) were combined, evaporated and re-evaporated with water to remove hydrogen chloride. There was obtained a crude residue of [(N-benzyloxycarbonyl-L-alanyl-L-alanyl)-amino]-methylphosphonic acid, which was converted to the benzylamine salt as follows:

The latter residue was taken up in water and titrated to pH 4.5 with 4-N benzylamine; liter 1.6 ml; theory 1.25 ml. The product crystallized on standing and was digested with warm water, cooled and stood overnight. The resulting precipitate was filtered off and washed with 25 ml of water until free from chloride ions [benzylamine hydrochloride]. The solid was washed successively with ethanol and ether and dried. There was obtained 1.085 g of the benzylamine salt of [(N-benzyloxycarbonyl-L-alanyl-L-alanyl)amino]-methylphosphonic acid of melting point 232°–234° C (decomposition); $[\alpha]_D^{20} = -22.1°$ ($c = 0.5\%$ in acetic acid). Concentration of the mother liquors gave a further 0.3 g of the benzylamine salt with a melting point of 232°–234° C (decomposition). Recrystallization of the first crop from 60 ml of water gave 0.71 g of pure benzylamine salt of melting point 232°–234° C (decomposition); $[\alpha]_D^{20} = -20.3°$ ($c = 0.5\%$ in acetic acid).

b. The process 28 g (0.057 mol) of the benzylamine salt of [N-benzyloxycarbonyl-L-alanyl-L-alanyl)amino]-methylphosphonic acid prepared according to part a) of this Example were dissolved in a minimum volume of 2-N ammonium hydroxide and passed down a cation exchange column (B.D.H., Zerolit 225, SRC 13, $RSO_3H$; 1.5 kg; freshly regenerated in the acid cycle) and eluted with water. There were collected 2 liters of acid eluate which were concentrated to 500 ml. To this were added 500 ml of methanol, 5 g of 10% palladium-on-charcoal catalyst and 0.2 ml of glacial acetic acid. The mixture was hydrogenated at room temperature and atmospheric pressure. The catalyst was filtered off and the solvent evaporated. The residue was evaporated four times with 250 ml batches of n-propanol and triturated with ether to give 12.46 g of a crude white solid of melting point 200°–265° C (decomposition). This white solid was recrystallized from 190 ml of water and 190 ml of ethanol by standing overnight at 0° C and subsequently filtering. There were obtained 8.69 g of (L-alanyl-L-alanyl-amino)-methylphosphonic acid of melting point 290°–292° C (decomposition); $[\alpha]_D^{20} = -38.6°$ ($c$ = 1% in water).

EXAMPLE 8

Preparation of the starting material

In a manner analogous to Example 7($a$), starting from the N-hydroxysuccinimide ester of N-benzyloxycarbonyl-L-alanine and (L-alanyl-L-alanylamino)-methylphosphonic acid there was obtained the benzylamine salt of [(N-benzyloxycarbonyl-L-alanyl-L-alanyl-L-alanyl)amino]-methylphosphonic acid of melting point 249°–251° C (decomposition); $[\alpha]_D^{20} = -32.2°$ ($c$ = 0.5% in acetic acid).

b. The process

In a manner analogous to Example 7($b$), starting from the benzylamine salt of [N-benzyloxycarbonyl-L-alanyl-L-alanyl-L-alanyl)amino]-methylphosphonic acid there was obtained (L-alanyl-L-alanyl-L-alanylamino)-methylphosphonic acid of melting point 323°–324° C (decomposition); $[\alpha]_D^{20} = -78.2°$ ($c$ = 0.5% in water).

EXAMPLE 9 a. Preparation of the starting material 2.8 g (0.036 mol) of solid sodium carbonate were added at 5° C to a solution of 1.96 g (0.018 mol) of (aminomethyl)methylphosphinic acid in 72 ml of water and 36 ml of ethanol, a clear solution resulting. The solution was stirred at 0° C while a warm solution of 5.76 g (0.018 mol) of the N-hydroxysuccinimide ester of N-benzyloxycarbonyl-L-alanine in 36 ml of ethanol was added and washed in with two 10 ml portions of warm ethanol. The heterogeneous mixture was stirred at 0° C for 2 hours and then overnight at room temperature. The mixture was evaporated and then re-evaporated with 50 ml of water to remove ethanol. The residue was dissolved in 150 ml of water and extracted once with 150 ml of chloroform and twice with 30 ml portions of chloroform. The aqueous layer was acidified with 18 ml of 2-N hydrochloric acid and again extracted once with 150 ml of chloroform and twice with 30 ml portions of chloroform. The aqueous layer was separated, evaporated and then taken up in 10 ml of water and 10 ml of 2-N ammonium hydroxide. The solution was passed down a column of cation exchange resin (B.D.H., Zerolit 225, SRC 13, RSO$_3$H; 150 g; freshly regenerated in the acid cycle) and eluted with water. There were collected four 100 ml acid fractions. The first two fractions were combined and evaporated to give a gum. This was re-evaporated with water to remove hydrogen chloride and there remained a sticky solid which was triturated with ether/dioxane (1:1). There were obtained 1.8 g of a white solid of melting point 118°–121° C (decomposition). Concentration of the mother liquors gave a further 2.02 g of solid of melting point 126°–130° C (decomposition). Recrystallization of the second crop from dioxane/ether gave 1.82 g of [(N-benzyloxycarbonyl-L-alanyl)amino]-methyl -methylphosphinic acid of melting point 129°–131° (decomposition); $[\alpha]_D^{20} = -26.0°$ ($c$ = 1% in water).

b. The process 1.5 g (0.005 mol) of [(N-benzyloxycarbonyl-L-alanyl)-amino]-methyl -methylphosphinic acid were dissolved in 75 ml of methanol and 75 ml of water. There were added successively 0.2 g of 5% palladium-on-charcoal catalyst and 5 drops of glacial acetic acid. The mixture was hydrogenated at room temperature and atmospheric pressure. The catalyst was filtered off and the solvent evaporated. The residue was re-evaporated three times with 50 ml portions of n-propanol to give ca 0.80 g of a white solid of melting point ca 146° C (decomposition). Recrystallization of this solid from 5 ml of methanol and 10 ml of acetone gave 0.63 g of [(L-alanyl-amino)methyl]-methylphosphinic acid of melting point ca 240° C (decomposition); hygroscopic; $[\alpha]_D^{20} = -26.9°$ ($c$ = 1% in water).

EXAMPLE 10 a. Preparation of the starting material 14.1 g (0.168 mol) of solid sodium bicarbonate were added to a solution of 7 g (0.056 mol) of (1R,S)-1-aminoethylphosphonic acid in 280 ml of water and 140 ml of ethanol while stirring at 0° C. While stirring this mixture at 0° C, a solution of 17.9 g (0.056 mol) of the N-hydroxysuccinimide ester of N-benzyloxycarbonyl-L-alanine in 140 ml of warm ethanol was added dropwise over ca 15 minutes. The latter solution was washed in with 70 ml of ethanol. The heterogeneous mixture was stirred for 1 hour at 0° C and then for a further 16 hours at room temperature, the mixture becoming homogeneous. The mixture was evaporated and re-evaporated with 200 ml of water to give a gum which was dissolved in 500 ml of water. The solution was extracted firstly with 500 ml of chloroform and then with 250 ml portions of chloroform, acidified to pH 2 with ca 80 ml of 2-N hydrochloric acid and again extracted with 500 ml of chloroform followed by two 250 ml portions of chloroform. The aqueous layer was concentrated and passed down a column of cation exchange resin (B.D.H., Zerolit 225, SRC 13, RSO$_3$H; 750 g; freshly regenerated in the acid cycle). The column was eluted with water and there were collected six 250 ml fractions. The first four fractions were combined, evaporated and re-evaporated with water to remove hydrogen chloride. There was obtained a final residue of (1R,S)-1-[(N-benzyloxxycarbonyl-L-alanyl)-amino]-ethylphosphonic acid which was separated as follows:

The latter residue was dissolved in 400 ml of water and titrated with 1-M benzylamine to pH 4.5; liter 75 ml; theory 56 ml. The resulting solution was concentrated and crystallized from water to give 5.3 g of the benzylamine salt of (1S)-1-[(N-benzyloxycarbonyl-L-alanyl)amino]-ethylphosphonic acid of melting point 210°–215° C. Concentration of the mother liquors followed by further recrystallization from water gave the benzylamine salt of (1R)-1-[(N-benzyloxycarbonyl-L-alanyl)amino]-ethylphosphonic acid in a first crop of 0.59 g [melting point 226°–228° C (decomposition); $[\alpha]_D^{20} = -32.3°$ ($c$ = 1% in acetic acid)] and a second crop of 0.825 g ]melting point 225°–227° C (decomposition); $[\alpha]_D^{20} = -33.0°$ ($c$ = 1% in acetic acid)]. Recrystallization of the first crop from water gave 0.333 g of pure benzylamine salt of the R-stereoisomer; melting point 226°–228° C (decomposition); $[\alpha]_D^{20} = -33.1°$ ($c$ = 1% in acetic acid).

b. The process 1.1 g (2.5 mmol) of the benzylamine salt of (1R)-1-[(N-benzyloxycarbonyl-L-alanyl)amino]-ethylphosphonic acid were dissolved in 4 ml of 2-N ammonium hydroxide, passed down a column of cation exchange resin (B.D.H., Zerolit 225, SRC 13, RSO$_3$H; 120 g; freshly regenerated in the acid cycle) and eluted with water. There were collected 200 ml of acid eluate which was concentrated to 100 ml. To this were added successively 100 ml of methanol, 0.3 g of 5% palladium-on-charcoal catalyst and 3 drops of glacial acetic acid. The mixture was hydrogenated at room temperature and atmospheric pressure. The catalyst was filtered off and the solvent evaporated. The residual gum was re-evaporated with three 50 ml portions of n-propanol to give 0.6 g of a gummy solid of melting point ca 275°–280° C (decomposition). After further recrystallization from water and ethanol, there was obtained 0.2 g of (1R)-1-(L-alanylamino)-ethylphosphonic acid of melting point 295°–296° (decomposition); $[\alpha]_D^{20} = -44.0°$ ($c = 1\%$ in water).

EXAMPLE 11 a. Preparation of the starting material

A solution of 30 g (0.24 mol) of (1R,S)-1-aminoethyl-phosphoric acid in 120 ml (0.48 mol) of 4-N sodium hydroxide was stirred at 14° C while 180 ml (0.72 mol) of a solution of 4-N sodium hydroxide and 102 g (0.60 mol) of benzyl chloroformate were added alternately in four portions. The stirring was continued and after a further 2 hours the temperature had risen to 20° C. The mixture was stirred for a further 16 hours at room temperature. 600 ml of ether were then added and the mixture was stirred vigorously for 2 hours to extract the excess benzyl chloroformate. The layers were separated and the aqueous layer was acidified to pH 2 with ca 110 ml of 5-N hydrochloric acid while maintaining the temperature below 10° C. The resulting slurry was concentrated to a low bulk to remove carbon dioxide. The residue was dissolved in 100 ml of 2-N sodium hydroxide and 50 ml of water, passed down a column of cation exchange resin (B.D.H., Zerolit 225 SRC 13, RSO$_3$H; 750 g; freshly regenerated in the acid cycle) and eluted with water. There were obtained ca 3.2 liters of acid eluate which were evaporated at room temperature and reevaporated with three 500 ml portions of water. The residue was dissolved in water and allowed to crystallize. The crystals were filtered off, washed with ice-cold water and dried; yield 39.2 g; melting point 111°–113° C (decomposition). Evaporation of the combined filtrates followed by crystallization from 75 ml of water and 10 ml of methanol and refrigeration, gave a further yield of 6.51 g; melting point 110°–112° C (decomposition). There was obtained a total of 45.71 g of (1R,S)-1-(benzyloxycarbonylamino)-ethylphosphonic acid, which was characterized as the monobenzylamine salt of melting point 196°–197° C (decomposition).

42.2 g (163 mmol) of (1R,S)-1-(benzyloxycarbonylamino)ethylphosphonic acid were dissolved in 100 ml of methanol. The solution was treated with a solution of 30.8 g (81.5 mmol) of quinine trihydrate in 100 ml of methanol and the mixture was stirred for 3 hours at room temperature and then overnight at 0° C. The quinine salt of (1S)-1-(benzyloxycarbonyl-amino)-ethylphosphonic acid was filtered off and washed with methanol. The combined filtrates were evaporated and the residue was dissolved in 300 ml of 2-N ammonium hydroxide. The solution was extracted with three 300 ml portions of chloroform. Each chloroform extract was back-washed with 150 ml of water. The aqueous extracts were combined, concentrated and then passed down a column of cation exchange resin (B.D.H., Zerolit 225, SRC 13, RSO$_3$H; 750 g; freshly regenerated in the acid cycle). Elution with water gave ca 2.3 liters of acid eluate, which was evaporated. The residue was re-evaporated firstly with three 200 ml portions of water and then with three 300 ml portions of methanol to give ca 24 g of a residual gum. This gum was dissolved in 100 ml of dry methanol and treated with a solution of dehydroabietylamine [82 mmol; freshly regenerated from 28.4 g (82 mmol) of dehydroabietylamine acetate with ammonium hydroxide/petroleum ether]. The mixture was stood at 0° C, filtered and the filtrate was washed with methanol and ether. There were obtained 47.4 g of crude dehydroabietylamine salt of (1R)-1-(benzyloxycarbonyl-amino)-ethylphosphonic acid of melting point 189°–194° C (decomposition); $[\alpha]D^{20} = +16.8°$($c = 0.5\%$ in methanol). Further recrystallization from methanol and water gave 33.0 g of the pure dehydroabietylamine salt of (1R)-1-(benzyloxycarbonyl-amino)-ethylphosphonic acid of melting point 202°–205° C (decomposition); $[\alpha]_D^{20} = +18.1°$ ($c = 0.5\%$ in methanol).

8.0 g (14 mmol) of the dehhydroabietylamine salt of (1R)-1-(benzyloxycarbonyl-amino)-ethylphosphonic acid were partitioned between 100 ml of 2-N ammonium hydroxide and 100 ml of petroleum ether (boiling point range 60°–80° C). The mixture was shaken vigorously and then the layers were separated. The aqueous layer was extracted with two 50 ml portions of petroleum ether. Each petroleum ether extract was then back-extracted with two 50 ml portions of water. The aqueous extracts were combined and evaporated at room temperature to give an oil. This oil was dissolved in water, passed down a column of cation exchange resin (B.D.H., Zerolit 225, SRC 13, RSO$_3$H;; 250 g; freshly regenerated in the acid cycle) and eluted with water. There were obtained 800 ml of an acid fraction which was then concentrated to 400 ml. To this concentrate were added successively 2.0 g of 10% palladium-on-charcoal catalyst, 400 ml of methanol and 0.2 ml of glacial acetic acid. The mixture was then hydrogenated. The catalyst was filtered off and the solvent evaporated. The residue was re-evaporated with three 100 ml portions of n-propanol and triturated with ether to give a solid of melting point ca 285°–288° C (decomposition). Recrystallization from water and ethanol gave 1.0 g of (1R)-1-aminoethylphosphonic acid of melting point 294°–295° C (decomposition); $[\alpha]_D^{20} = -16.9°$ ($c = 2\%$ in 1-N sodium hydroxide).

0.4 g (3.2 mmol) of (1R)-1-aminoethylphosphonic acid in 14 ml of water and 7 ml of ethanol were stirred at 10° C while 0.806 g (9.6 mmol) of sodium bicarbonate were added portion-wise. The mixture was then stirred at 0° C while a hot solution of 1.024 g (3.2 mmol) of the N-hydroxysuccinimide ester of N-benzyloxycarbonyl-L-alanine in 8 ml of ethanol was added rapidly dropwise. The mixture was stirred for 3 hours at 0° C and then for 16 hours at room temperature. The mixture was worked up in a manner analogous to Example 10(a) by passing down a column of cation exchange resin and converting to the benzylamine salt. There were obtained 0.26 g of the benzylamine salt of (1R)-1-[(N-benzyloxycarbonyl-L-alanyl)amino]-ethylphosphonic acid of melting point 229°–231° C (decomposition); $[\alpha]_D^{20} = -34.2°$ ($c = 1\%$ in glacial acetic acid).

b. The process:

In a manner analogous to Example 10(b), starting from the benzylamine salt of (1R)-1-[(N-benzyloxycarbonyl-L-alanyl)-amino]-ethylphosphonic acid there was obtained (1R)-1-(L-alanylamino)-ethylphosphonic acid of melting point 295°–296° C (decomposition); $[\alpha]_D^{20} = -45.6°$ ($c = 1\%$ in water).

EXAMPLE 12 a. Preparation of the starting material

In a manner analogous to Example 7(a), starting from the N-hydroxysuccinimide ester of N-benzyloxycarbonyl-L-alanine and (1R)-1-(L-alanylamino)-ethylphosphonic acid there was obtained the benzylamine salt of (1R)-1-[(N-benzyloxycarbonyl-L-alanyl-L-alanyl)amino]-ethylphosphonic acid of melting point 247°–250° C (decomposition); $[\alpha]_D^{20} = -45.1°$ ($c = 0.5\%$ in acetic acid).

b. The process

In a manner analogous to Example 7(b), starting from the benzylamine salt of (1R)-1-[(N-benzyloxycarbonyl-L-alanyl-L-alanyl)amino]-ethylphosphonic acid there was obtained (1R)-1-(L-alanyl-L-alanylamino)-ethylphosphonic acid of melting point 283°–284° C (decomposition); $[\alpha]_D^{20} = -66.8°$ ($c = 0.5\%$ in water).

EXAMPLE 13 a. Preparation of the starting material 9.6 g (0.03 mol) of the N-hydroxysuccinimide ester of N-benzyloxycarbonyl-L-alanine and 5.26 g (0.03 mol) of dimethyl aminomethylphosphonate hydrochloride were stirred in 65 ml of dry dimethylformamide. While stirring and maintaining the temperature below 20° C, there were added dropwise 4.2 ml of dry triethylamine. The mixture was then stirred overnight at room temperature. The triethylamine hydrochloride was filtered off and washed with a little dimethylformamide. The filtrate was evaporated under an oil-pump vacuum and at a bath temperature below 40° C. The residual oil was treated with 40 ml of water and the resulting mixture extracted with four 40 ml portions of chloroform. The combined organic phases were washed with a small volume of a strong potassium carbonate solution and then dried over sodium sulphate. The sodium sulphate was filtered off and the filtrate evaporated first under a water-pump vacuum and then under an oil-pump vacuum. There were obtained 11.0 g of dimethyl [(N-benzyloxycarbonyl-L-alanyl)amino]-methylphosphonate as an oil with the expected N.M.R. spectrum.

The process 11.0 g of dimethyl [(N-benzyloxycarbonyl-L-alanyl)-amino]-methylphosphonate were dissolved in 40 ml of a 35% solution of hydrogen bromide in glacial acetic acid and the mixture was stirred at room temperature for 2 hours. 300 ml of ether were then added while stirring, the stirring was discontinued and the ether decanted. This was repeated with 200 ml of ether and then 100 ml of ether. The residue was dissolved in 50 ml of methanol and to the resulting solution was added a solution of 6 ml of propylene oxide in 10 ml of methanol. After standing for several hours, the resulting white precipitate was filtered off and washed with methanol and ethanol. The product was dried to a constant weight of 4.60 g (84% overall yield); melting point 289°–291° C (decomposition). Recrystallization from 20 ml of boiling water by the addition of 30 ml of ethanol, gave 4.03 g of (L-alanyl-amino)-methylphosphonic acid of melting point 294°–296° C (decomposition); $[\alpha]_D^{20} = +31.0°$ ($c = 1\%$ in water);

EXAMPLE 14 a. Preparation of the starting material

In a manner analogous to Example 13(a), starting from the N-hydroxysuccinimide ester of N-benzyloxycarbonyl-L-alanine and diethyl aminomethylphosphonate hydrochloride there was obtained diethyl [(N-benzyloxycarbonyl-L-alanyl)amino]-methylphosphonate as a solid of melting point 72°–74° C.

b. The process

In a manner analogous to Example 13(b), but with reaction of diethyl [(N-benzyloxycarbonyl-L-alanyl)amino]-methylphosphonate and hydrogen bromide/glacial acetic acid for 22 hours, there was obtained (L-alanylamino)-methylphosphonic acid of melting point 293°–294° C (decomposition); $[\alpha]_D^{20} = +31.8°$ ($c = 1\%$ in water).

EXAMPLE 15 a. Preparation of the starting material

In a manner analogous to Example 13(a), starting from the N-hydroxysuccinimide ester of N-benzyloxycarbonyl-L-phenylalanine and dimethyl aminomethylphosphonate hydrochloride there was obtained dimethyl [(N-benzyloxycarbonyl-L-phenylalanyl)amino]-methylphosphonate as an oil with the expected N.M.R. spectrum.

b. The process

In a manner analogous to Example 13(b), but with reaction of dimethyl [(N-benzyloxycarbonyl-L-phenylalanyl)-amino]-methylphosphonate and hydrogen bromide/glacial acetic acid for 2 hours, there was obtained (L-phenylalanylamino)methylphosphonic acid of melting point 266°–268° C (decomposition); $[\alpha]_D^{20} = +74.5°$ ($c = 0.8\%$ in water).

EXAMPLE 16 a. Preparation of the starting material

In a manner analogous to Example 13(a), starting from the N-hydroxysuccinimide ester of N-benzyloxycarbonyl-L-leucine and dimethyl aminomethylphosphonate hydrochloride there was obtained dimethyl [(N-benzyloxycarbonyl-L-leucyl)amino]-methylphosphonate as a crystalline solid of melting point 90°–91° C; $[\alpha]_D^{20} = -24.3°$ ($c = 1\%$ in methanol).

b. The process

In a manner analogous to Example 13(b), but with reaction of dimethyl [(N-benzyloxycarbonyl-L-leucyl)amino]-methylphosphonate and hydrogen bromide/glacial acetic acid for 2 hours, there was obtained (L-leucylamino)-methylphosphonic acid of melting point firstly at 262°–264° C (decomposition) and, after recrystallization from aqueous methanol, finally at 263°–265° C (decomposition); $[\alpha]_D^{20} = +62.2°$ ($c = 1\%$ in water).

EXAMPLE 17 a. Preparation of the starting material

In a manner analogous to Example 13(a) starting from 64.0 g of the N-hydroxysuccinimide ester of N-benzyloxycarbonyl-L-alanine and 35.1 g of dimethyl aminomethylphosphonate hydrochloride, there were obtained 73.3 g of dimethyl [(N-benzyloxycarbonyl-L-alanyl)amino]-methylphosphonate as an oil. This oil was refluxed in a mixture of 200 ml of trimethylchlorosilane and 100 ml of acetonitrile under exclusion of moisture for 100 hours. The mixture was then cooled, filtered and evaporated in vacuo on a rotary evaporator. The residue was re-evaporated several times with toluene. The final residue was dissolved in 250 ml of dioxane and treated with 25 ml of water. Crystallization began after several minutes and this was completed by storing overnight. The separated solid was filtered off, washed with ethyl acetate and dried in vacuo. There were obtained 29.0 g of solid of melting point 147°–148° C (decomposition). A further 28.0 g of solid of the same melting point were obtained by concentration of the mother liquors and treatment with ethyl acetate. The combined solids were recrystallized by dissolving in 1.5 parts by volume of tepid methanol, filtering and then adding 15 parts by volume of ethyl acetate to the filtrate. There were obtained 39.5 g of pure [(N-benzyloxycarbonyl-L-alanyl)amino]-methylphosphonic acid of melting point 153°–155° C (decomposition); $[\alpha]_D^{20} = -28.9°$ (c = 1% in water).

The process 63.2 g of [(N-benzyloxycarbonyl-L-alanyl)amino]-methylphosphonic acid in a mixture of 600 ml of methanol and 20 ml of concentrated hydrochloric acid were hydrogenated at room temperature and atmospheric pressure in the presence of 6.0 g of 10% palladium-on-charcoal catalyst until absorption of hydrogen ceased. The catalyst was filtered off and washed with methanol. The filtrate was treated with 30 ml of propylene oxide and the mixture stored overnight in a refrigerator. The solid was filtered off, washed with methanol and ether and dried over phosphorus pentoxide in vacuo. The solid was taken up in 80 ml of boiling water, filtered and treated with 120 ml of ethanol. The mixture was cooled and then refrigerated overnight. The solid was filtered off, washed well with ethanol and dried over phosphorus pentoxide in vacuo. There were obtained 31.85 g of (L-alanylamino)-methylphosphonic acid of melting point 293°–294° C (decomposition); $[\alpha]_D^{20} = 33.8°$ (c =1% in water).

EXAMPLE 18 a. Preparation of the starting material

In a manner analogous to Example 17 (a), starting from the N-hydroxysuccinimide ester of N-benzyloxycarbonyl-L-phenylalanine and dimethyl aminomethylphosphonate hydrochloride there was obtained [(N-benzyloxycarbonyl-L-phenyl-alanyl)amino]-methyl-phosphonic acid of melting point 183°–184° C (decomposition); $[\alpha]_D^{20} = -10.9°$ (c =1% in methanol).

b. The process

In a manner analogous to Example 17 (b), starting from [(N-benzyloxycarbonyl-L-phenylalanyl)amino]-methylphosphonic acid there was obtained (L-phenylalanylamino)-methylphosphonic acid of melting point 264°–266° C (decomposition); $\alpha]=+76.2°$ (c =1% in water).

EXAMPLE 19 a. Preparation of the starting material

In a manner analogous to Example 17 (a), starting from the N-hydroxysuccinimide ester of N-benzyloxycarbonyl-L-leucine and dimethyl aminomethylphosphonate hydrochloride there was obtained [(N-benzyloxycarbonyl-L-leucyl)amino]-methyl-phosphonic acid of melting point 129°–130° C; $[\alpha]_D^{20} = -29.2°$ (c =1% in water).

b. The process

In manner analogous to Example 17 (b), starting from [(N-benzyloxycarbonyl-L-leucyl)amino]-methylphosphonic acid there was obtained (L-leucylamino)-methylphosphonic acid of melting point 263 –265° C (decomposition); $[\alpha]_D^{20} =+62.2°$ (c =1% in water).

EXAMPLE 20 a. Preparation of the starting material:

In a manner analogous to Example 13 (a), starting from 64.0 g of the N-hydroxysuccinimde ester of N-benzyloxy-carbonyl-L-alanine and 35.1 g of dimethyl aminomethylphosphonate hydrochloride, there were obtained 73.3 g of dimethyl [(N-benzyloxycarbonyl-L-alanyl)amino]-methylphosphonate as an oil. This oil was dissolved in 350 ml of methanol and treated with 40 ml of 5 -N methanolic hydrogen chloride. The mixture was then hydrogenated for several hours at room temperature under atmospheric pressure and a soda-lime trap and in the presence of 6 g of 10% palladium-on-charcoal catalyst until hydrogen uptake ceased. The catalyst was filtered off and the filtrate evaporated in vacuo to 100 ml. After the addition of 300 ml of ethyl acetate, crystallization began and was completed by storing overnight at 0° C. The solid was filtered off, washed successively with ethyl acetate/methanol and ethyl acetate and then dried in vacuo. There were obtained 40.9 g of solid which was recrystallized from methanol/ethyl acetate to yield 40.5 g of dimethyl (L-alanylamino)-methylphosphonate hydrochloride or melting point 168°–170° C (decomposition); $[\alpha]_D^{20} = -5.05°$ (c =1% in water).

24.65 g of dimethyl (L-alanylamino)-methylphosphonate hydrochloride and 32.0 g of the N-hydroxysuccinimide ester of N-benzyloxycarbonyl-L-alanine were stirred in 200 ml of dry dimethylformamide while 14 ml of dry triethylamine were added dropwise at 20° C. The mixture was stirred overnight and then the triethylamine hydrochloride filtered off and washed with a small amount of dimethylformamide. The filtrate was evaporated under an oil-pump vacuum, the residue treated with 150 ml of water and then extracted with four 125 ml portions of chloroform. The combined chloroform layers were washed with a 20 % potassium carbonate solution, separated and dried over sodium sulphate. The sodium sulphate was filtered off, the filtrate evaporated firstly under a water-pump vacuum and then under an oil-pump vacuum and the residue taken up in 100 ml of ethyl acetate. About 100 ml of ether were added to faint turbidity when crystallization began. After refrigeration overnight, the solid was filtered off, washed successively with ethyl acetate/ether (1:1) and ether and then dried in vacuo. Recrystallization from 200 ml of boiling ethyl acetate by the addition of 200 ml of ether gave 27.8 g of dimethyl [(N-benzyloxycarbonyl-L-alanyl-L-alanyl)amino]-methyl-phosphonate of melting point 106°–108° C; $[\alpha]_D^{20} = -37.4°$ (c =1% in glacial acetic acid).

b. The process 4.05 g of dimethyl [(N-benzyloxycarbonyl-L-alanyl-L-alanyl)amino]-methylphosphonate were stirred in 14 ml of a solution of 35 % w/v hydrogen bromide in glacial acetic acid for 3 hours. 100 ml of ether were added and the mixture was stirred for a few minutes and then stood. The supernatant ether was decanted and the residual gum was treated similarly with two further 50 ml portions of ether. The residue was dissolved in 15 ml of methanol and treated with 2.5 ml of propylene oxide. A solid separated almost immediately. After refrigeration for 1 hour, the mixture was filtered and the solid washed with methanol and dried in vacuo. After recrystallization from water/ethanol, there were obtained 1.91 g of (L-alanyl-L-alanylamino)-methylphosphonic acid of melting point 280°–281° C (decomposition); $[\alpha]_D^{20} = -40.0°$ ($c = 1\%$ in water).

EXAMPLE 21 a. Preparation of the starting material

In a manner analogous to Example 20 (a), from dimethyl (L-anlanylamino)-methylphosphonate hydrochloride and the N-hydroxysuccinimide ester of N-benzyloxycarbonyl-L-leucine there was obtained dimethyl [(N-benzyloxycarbonyl-L-leucyl-L-alanyl)amino]-methylphosphonate of melting point 117°–119° C; $[\alpha]_D^{20} = -42.55°$ ($c = 1\%$ in methanol).

b. The process:

In a manner analogous to Example 20 (b), from dimethyl [(N-benzyloxycarbonyl-L-leucyl-L-alanylamino]-methylphosphonate there was obtained (L-leucyl-L-alanylamino)-methylphosphonic acid of melting point 263°–265° C (decomposition); $[\alpha]_D^{20} = -12.8°$ ($c = 1\%$ in water).

EXAMPLE 22 a. Preparation of the starting material

In a manner analogous to Example 20 (a), from dimethyl (L-leucylamino)-methylphosphonate hydrochloride and the N-hydroxysuccinimide ester of N-benzyloxycarbonyl-L-alanine there was obtained dimethyl [(N-benzyloxycarbonyl-L-alanyl-L-leucyl)amino]-methylphosphonate of melting point 163°–165° C; $[\alpha]_D^{20} = -51.6°$ ($c = 1\%$ in methanol).

b. The process

In a manner analogous to Example 20 (b), from dimethyl [(N-benzyloxycarbonyl-L-alanyl-L-leucyl)-amino]-methylphosphonate there was obtained (L-alanyl-L-leucylamino)-methylphosphonic acid melting point 263°–264° C (decomposition); $[\alpha]_D^{20} = -23.4°$ ($c = 1\%$ in water).

EXAMPLE 23 a. Preparation of the starting material:

In a manner analogous to Example 20 (a), but using the 2,4,5-trichlorophenyl ester of N-benzyloxycarbonyl-L-alanine instead of the N-hydroxysuccinimide ester, there was obtained dimethyl [(N-benzyloxcarbonyl-L-alanyl-L-alanyl)amino]-methylphosphonate of melting point 106°–108° C; $[\alpha]_D^{20} = -36.7°$ ($c = 1\%$ in glacial acetic acid).

b. The process

In a manner analogous to Example 20 (b), from dimethyl [(N-benzyloxycarbonyl-L-alanyl-L-alanyl)-amino]-methylphosphonate there was obtained (L-alanyl-L-alanyamino)-methylphosphonic acid of melting point 281°–282° C (decomposition); $[\alpha]_D^{20} = -39.8°$ ($c = 1\%$ in water).

EXAMPLE 24 a. Preparation of the starting material

In a manner analogous to the first part of Example 20 (a), from the N-hydroxysuccinimide ester of N-benzyloxycarbonyl-L-alanine and dimethyl aminomethylphosphonate hydrochloride there was obtained dimethyl (L-alanylamino)-methylphosphonate hydrochloride.

b. The process 4.93 g of dimethyl (L-alanylamino)-methylphosphonate hydrochloride were stirred in 27 ml of a 35 % solution of hydrogen bromide in glacial acetic acid for 3 hours. The mixture was worked up in an analogous manner to Example 13 (b). There were obtained 3.04 g of (L-alanylamino)-methylphosphonic acid of melting point 294°–295° C (decomposition); $[\alpha]_D^{20} = +30.3°$ ($c = 1\%$ in water).

EXAMPLE 25 a. Preparation of the starting material 139.7 g (0.5 mol) of dimethyl 1-benzylaminoethyl phosphonate hydrochloride were dissolved in 1000 ml of methanol. The solution was hydrogenated at room temperature and atmospheric pressure in the presence of 15 g of 10% palladium-on-charcoal for several hours until the hydrogen uptake ceased. The catalyst was filtered off and the filtrate evaporated in vacuo. The residue of dimethyl 1-aminoethylphosphonate hydrochloride was dissolved in 500 ml of dry dimethylformamide and then treated with 160 g (0.5 mol) of the N-hydroxysuccinimide ester of N-benzyloxycarbonyl L-alanine. While stirring and maintaining the temperature below 0° C, there were added dropwise 70 ml of dry triethylamine. The mixture was then stirred overnight at room temperature.

Further processing analogous to that given in Example 13 (a) yielded a residue which, on treatment with 600 ml of dry ether, gave 72.5 g of dimethyl(1S)-1-[(N-benzyloxycarbonyl-L-alanyl)amino]-ethylphosphonate of melting point 134°–135° C; $[\alpha]_D^{20} = +14.9°$ ($c = 1\%$ in methanol). Evaporation of the mother liquors gave ca 100 g of a gum consisting substantially of the corresponding R-isomer.

b. The process:

100 g of the gum obtained according to part a) were treated with 250 ml of a 45% solution of hydrogen bromide in glacial acetic acid for 5 hours at room temperature. 750 ml of ether were then added while stirring, the stirring was discontinued and the ether decanted. This procedure was repeated with two further 250 ml portions of ether. The residue was dissolved in 250 ml of methanol and to the resulting solution was added a solution of 50 ml of propylene oxide in 50 ml of methanol. After standing for several hours, the resulting precipitate was filtered off and washed with methanol and ether. The product was dried to a constant weight of 46.1 g and then had a melting point of 283°–285° C (decomposition). Recrystallization from water/ethanol mixtures yielded 36.5 g of (1R)-1-(L-alanylamino)-ethylphosphonic acid of melting point 295°–296° C (decomposition); $[\alpha]_D^{20} = -46.3°$ ($c = 1\%$ in water).

EXAMPLE 26 a. Preparation of the starting material

In a manner analogous to that given in Example 13 (a), from the N-hydroxysuccinimide ester of N-benzyloxycarbonyl-L-alanine and dimethyl 1-aminobenzylphosphonate hydrochloride, there was obtained an isomeric mixture. After chromatography on silica gel with an isopropanol/ethyl acetate eluant, followed by recrystallization from ethyl acetate/ether, there were isolated dimethyl (1S)-1-[(N-benzyloxycarbonyl-L-alanyl)-amino]-benzylphosphonate of melting point 103°–105° C [$[\alpha]_D^{20} = -46.6°$ ($c = 1\%$ in methanol)] and dimethyl (1R)-1-[(N-benzyl-oxycarbonyl-L-alanyl)]- benzylphosphonate of melting point 120°–122° C [$[\alpha]_D^{20}$ =+12.3°($c$ = 1% in methanol)]

b. The process

In a manner analogous to that given in Example 13 (*b*), from dimethyl (1R)-1-[(N-benzyloxycarbonyl-L-alany)amino]-benzylphosphonate there was obtained (1R)-1-(L-alanylamino)-benzylphosphonate acid of melting point 251°–252° C (decomposition); $[\alpha]_D^{20}$ =+69.1°($c$ = 1% in water).

EXAMPLE 27 a. Preparation of the starting material 100 g of the gum obtained according to Example 25 *a*) were dissolved in 500 ml of methanol containing 0.3 mol of hydrogen chloride. The solution was hydrogenated at room temperature and atmospheric pressure in the presence of 8 g of 10% palladium-on-charcoal until hydrogen uptake ceased. The catalyst was filtered off, the filtrate evaporated in vacuo and the residue triturated with acetone. The solid was filtered off, washed with acetone and dried in vacuo. After recrystallization from methanol/ether, there were obtained 42 g of dimethyl (1R)-1-(L-alanylamino)-ethylphosphonate hydrochloride of melting point 195°–198° C (decomposition); $[\alpha]_D^{20}$ =–51.1°($c$ = 1% in water).

In a manner analogous to that given in Example 13 (*a*), from 13 g of dimethyl (1R)-1-(L-alanylamino-ethylphosphonate hydrochloride and 16 g of the N-hydroxysuccinimide ester of N-benzyloxycarbonyl-L-alanine there were obtained 16 g of dimethyl (1R)-1-[(N-benzyloxycarbonyl-L-alanyl-L-alanyl)amino]-ethylphosphonate of melting point 149°–151° C; $[\alpha]_D^{20}$ =–65.5°($c$ = 1% in methanol).

b. The process

In a manner analogous to that given in Example 13 (*b*), from dimethyl (1R)-1-[(N-benzyloxycarbonyl-L-alanyl-L-alanyl)amino]ethylphosphonate there was obtained (1R)-1-(L-alanyl-L-alanylamino)-ethylphosphonate acid of melting point 279°–280° C (decomposition); $[\alpha]_D^{20}$ =–70.1°($c$ = 1% in water).

EXAMPLE 28 a. Preparation of the starting material:

In a manner analogous to that given in Example 27 (*a*), from dimethyl (1R)-1-(L-alanylamino)-ethylphosphonate hydrochloride and the N-hydroxysuccinimide ester of N-benzyloxycarbonylglycine there was obtained dimethyl (1R)-1-[(N-benzyloxycarbonyl-glycyl-L-alanyl)amino]-ethylphosphonate as an oil with the expected N.M.R. spectrum.

b. The process

In a manner analogous to that given in Example 13 (*b*), from dimethyl (1R) -[(N-benzyloxycarbonyl-glycyl-L-alanyl)amino]-ethylphosphonate there was obtained (1R)-1-(glycyl-L-alanylamino)-ethylphosphonate acid of melting point 289°–291° C (decomposition); $[\alpha]_D^{20}$ =–93.7°($c$ = 1% in water).

EXAMPLE 29 a. Preparation of the starting material:

In a manner analogous to that given in Example 27 (*a*), from dimethyl (1R)-1-(L-alanylamino)-ethylphosphonate hydrochloride and the N-hydroxysuccinimide ester of N-benzyloxycarbonyl-L-prolone there was obtained dimethyl (1R)-1-[(N-benzyloxycarbonyl-L-prolyl-L-alanyl)amino]-ethylphosphonate as an oil with the expected N.M.R. spectrum.

b. The process

In a manner analogous to that given in Example 13 (b), from dimethyl (1R)-1-[(N-benzyloxycarbonyl-L-prolyl-L-alanyl)amino]-ethylphosphonate there was obtained (1R)-1-(L-prolyl-L-alanylamino)-ethylphosphonate acid hemihydrate of melting point 263°–265° C (decomposition); $[\alpha]_D^{20}$ =–101.7°($c$ = 1% in water).

EXAMPLE 30 a. Preparation of the starting material:

In a manner analogous to that given in Example 27 (*a*), from dimethyl (1R)-1-[(N-benzyloxycarbonyl-L-alanyl-L-alanyl)amino]-ethylphosphonate there was obtained as a gum dimethyl (1R)-1-(L-alanyl-L-alanylamino)-ethylphosphonate hydrochloride. The latter compound was processed with the N-hydroxysuccinimide ester of N-benzyloxycarbonylglycine in a manner analogous to Example 13 (*a*) to yield dimethyl (1R)-1-[(N-benzyloxycarbonyl-glycyl-L-alanyl-L-alanyl)amino]-ethylphosphonate of melting point 162°–164° C; $[\alpha]_D^{20}$ =–55.0°($c$ = 1% in methanol).

b. The process

In a manner analogous to that given in Example 13 (*b*), from dimethyl (1R)-1-[(N-benzyloxycarbonyl-glycyl-L-alanyl-L-alanyl)amino]-ethylphosphonate there was obtained (1R)-1-(glycyl-L-alanyl-L-alanylamino)-ethylphosphonate acid of melting point 314°–316° C (decomposition); $[\alpha]_D^{20}$ =–97.5°($c$ = 1% in 1N sodium hydroxide).

EXAMPLE 31 a. Preparation of the starting material

In a manner analogous to that given in Example 30 *a*), from dimethyl (1R)-1-(L-alanyl-L-alanylamino)-ethylphosphonate hydrochloride and the N-hydroxysuccinimide ester of N-benzyloxycarbonyl-L-proline there was obtained dimethyl (1R)-1-[(N-benzyloxycarbonyl-L-prolyl-L-alanyl-L-alanyl)amino]-ethylphosphonate of melting point 181°–183° C; $[\alpha]_D^{20}$ =–100.3°($c$ = 1% in methanol).

b. The process

In a manner analogous to that given in Example 13 (*b*), from dimethyl (1R)-1-[(N-benzyloxycarbonyl-L-prolyl-L-alanyl-L-alanyl)amino]-ethylphosphonate there was obtained (1R)-1-(L-prolyl-L-alanyl-L-alanylamino)-ethylphosphonic acid of melting point 305°–306° C (decomposition); $[\alpha]_D^{20}$ =–134.4°($c$ = 1% in water).

EXAMPLE 32 a. Preparation of the starting material

In a manner analogous to that given in Example 27 *a*), from dimethyl (1R)-1-[(N-benzyloxycarbonyl-glycyl-L-alanyl)amino]-ethylphosphonate there was obtained dimethyl (1R)-1-(glycyl-L-alanylamino)-ethylphosphonate hydrochloride. The latter compound was processed with the N-hydroxysuccinimide ester of N-benzyloxycarbonylglycine in a manner analogous to Example 13 (*a*) to yield dimethyl (1R)-1-[(N-benzyloxycarbonyl-glycyl-glycyl-L-alanyl)amino]-ethylphosphonate of melting point 124°–127° C; $[\alpha]_D^{20}$ = –36.6°($c$ = 1% in methanol).

The process

In a manner analogous to that given in Example 13 (*b*), from dimethyl (1R)-1-[(N-benzyloxycarbonyl-glycyl-glycyl-L-alanyl)amino]-ethylphosphonate there was obtained (1R)-1-(glycyl-glycyl-L-alanylamino)-ethylphosphonic acid of melting point 288°–289° C (decomposition); $[\alpha]_D^{20} = -61.5°(c = 1\%$ in 0.1-N sodium hydroxide).

EXAMPLE 33

Preparation of the starting material

In a manner analogous to that given in Example 2 a), by reaction of (1R,S)-1-aminoethylphosphonic acid with the mixed anhydride obtained from N-benzyloxycarbonylglycine and isobutyl chloroformate there was obtained the benzylamine salt of (1R,S)-1-[(N-benzyloxycarbonyl-glycyl)amino]-ethylphosphonic acid of melting point 204°-206° C (decomposition).

2.1 g of the latter compound were converted to the free acid by ion exchange. The resulting acid was titrated with (+)-α-methylbenzylamine to pH 4.0, evaporated and then reevaporated with methanol. The residue was crystallized from a mixture of 10 ml of methanol and 0.5 ml of water at 0° C to give 0.85 g of the crude (+)-α-methylbenzylamine salt of melting point 202°-203° C (decomposition). Recrystallization from butanol/water gave the (+)-α-methylbenzylamine salt of (1R)-1-[(N-benzyloxycarbonyl-glycyl)amino]-ethylphosphonic acid of melting point 203°-204° C (decomposition); $[\alpha]_D^{20} = 14.8°(c = 0.9\%$ in water).

b. The process

In the manner analogous to that given in Example 1 (b), from the (+)-α-methylbenzylamine salt of (1R)-1-[(N-benzyloxycarbonyl-glycyl)amino]-ethylphosphonic acid there was obtained (1R)-1-glycylaminoethylphosphonic acid of melting point 277°-280° C (decomposition); $[\alpha]_D^{20} = -69.6°(c = 1\%$ in water).

EXAMPLE 34 a. Preparation of the starting material 2.5 g (20mol) of (1R)-1-aminoethylphosphonic acid were stirred in 5 ml of water at 0° C while 5.6 ml (40mmol) of triethylamine and 10 ml of dimethylformamide were added. 7.65 g (25mmol) of solid N-hydroxysuccinimide ester of N-benzyloxycarbonylglycine were added in a single portion. The mixture was stirred for 3 hours at 0° C and then for 16 hours at room temperature. The mixture was worked up in a manner analogous to that given in Example 11 (a). There were obtained 4.3 g of the benzylamine salt of (1R)-1-[(benzyloxycarbonyl-glycyl)amino]-ethylphosphonic acid of melting point 198°-200° C (decomposition); $[\alpha]_D^{20} = -16.6°(c = 1\%$ in water).

b. The process

In a manner analogous to that given in Example 1 (b), from the benzylamine salt of (1R)-1-[(benzyloxycarbonyl-glycyl)amino]-ethylphosphonic acid there was obtained (1R)-1-glycylamino-ethylphosphonic acid of melting point 279°-281° C (decomposition); $[\alpha]_D^{20} = -69.4°(c = 1\%$ in water).

EXAMPLE 35 a. Preparation of the starting material:

0.88 g (7.0mmol) of (1R)-1-aminoethylphosphonic acid were stirred in 100 ml of water at 5° C while 1.41 g (14mmol) of triethylamine and 100 ml of ethanol were added. 2.42 g (7.0mmol) of solid N-hydroxysuccinimide ester of N-benzyloxycarbonyl-L-proline were added and washed in with 50 ml of ethanol. The mixture was stirred at 0° C for 2 hours and then at room temperature for 72 hours. The mixture was worked up in essentially the same manner as given in Example 11 a). After recrystallization from methanol/ether, there were obtained 2.3g of the benzylamine salt of (1R)-1-[(N-benzyloxycarbonyl-L-prolyl)amino]-ethylphosphonic acid of melting point 206°-209° C (decomposition); $[\alpha]_D^{20} = -53.1°(c = 0.6\%$ in glacial acetic acid).

b. The process 2.3 of the benzylamine salt of (1R)-1-[(N-benzyloxycarbonyl-L-prolyl)amino]-ethylphosphonic acid were added to a stirred solution (45%) of hydrogen bromide in glacial acetic acid and washed in with 2.5 ml of glacial acetic acid. The mixture was stirred at room temperature for 6 hours and then 75ml of ether were added while stirring. The supernatant was decanted and the residue was again treated with 75ml of ether. The granular solid obtained was dissolved in 30ml of methanol and the solution treated with a solution of 5ml of propylene oxide in 10ml of methanol. After standing for several hours, the precipitate was filtered off, washed with methanol and ether and dried. Crystallization from water/ethanol gave 0.39 g of (1R)-1-(L-prolylamino)-ethylphosphonic acid of melting point 291°-293° C (decomposition); $[\alpha]_D^{20} = -92.3°(c = 0.5\%$ in water).

EXAMPLE 36 a. Preparation of the starting material

In a manner analogous to that given in Example 34a), from the N-hydroxysuccinimide ester of $N^2$, $N^6$-bis(benzyloxy-carbonyl)-L-lysine there was obtained (1R)-1-[($N^2$, $N^6$-bis(benzyloxycarbonyl)-L-lysyl)amino]-ethylphosphonic acid of melting point 195°-197° C (decomposition); $[\alpha]_D^{20} = -17.5°(c = 0.5\%$ in ethanol).

b. The process

In a manner analogous to that given in Example 1b), from (1R)-1-[($N^2$, $N^6$-bis (benzyloxycarbonyl)-L-lysyl)amino]ethylphosphonic acid there was obtained (for improved crystallization) the acid oxalate salt of (1R)-1-(L-lysylamino)-ethylphosphonic acid of melting point 265° C (decomposition); $[\alpha]_D^{20} = -10.4°(c = 0.5\%$ in water).

EXAMPLE 37 a. Preparation of the starting material:

In a manner analogous to that given in Example 34 (a), from the N-hydroxysuccinimide ester of N-benzyloxycarbonyl-L-leucine there was obtained the benzylamine salt of (1R)-1-[(N-benzyloxycarbonyl-L-leucyl)amino]-ethyphosphonic acid of melting point 228°-230° C (decomposition); $[\alpha]_D^{20} = -32.0°(c = 0.5\%$ in glacial acetic acid).

b. The process

In a manner analogous to that given in Example 1 (b), from the benzylamine salt of (1R)-1-[(N-benzyloxycarbonyl-L-leucyl)amino]-ethylphosphonic acid there was obtained (1R)-1-(L-leucylamino)-ethylphosphonic acid of melting point 238°-240° C (decomposition); $[\alpha]_D^{20} = -14.2°$ $(c = 0.5\%$ in water).

EXAMPLE 38 a. Preparation of the starting material

From N-benzyloxycarbonyl-L-valine, N-ethylmorpholine and (1R)-1-aminoethylphosphonic acid there was obtained in a manner analogous to that given in Example 2 (a) the benzylamine salt of (1R)-1-[(N-benzyloxycarbonyl-L-valyl)amino]-ethylphosphonic acid of melting point 251°-252° C (decomposition); $[\alpha]_D^{20} = -25.4°$ $(c = 0.5\%$ in glacial acetic acid).

b. The process

In a manner analogous to that given in Example 35 (b), from the benzylamine salt of (1R)-1-[(N-benzyloxycarbonyl-L-valyl)amino]-ethylphosphonic acid there was obtained (1R)-1-(L-valylamino)-ethylphosphonic acid of melting point 276°–277° C (decomposition); $[\alpha]_D^{20} = -9.3°$ (c = 0.5% in water).

EXAMPLE 39 a. Preparation of the starting material

In a manner analogous to that given in Example 34 (a), from the N-hydroxysuccinimide ester of N-benzyloxycarbonyl-L-phenylalanine there was obtained (1R)-1-[(N-benzyloxycarbonyl-L-phenylalanyl)amino]-ethylphosphonic acid of melting point 212°–215° C (decomposition); $[\alpha]_D^{20} = -16.3°$ (c = 0.5% in ethanol).

b. The process

In a manner analogous to that given in Example 1 (b), from (1R)-1-[(N-benzyloxycarbonyl-L-phenylalanyl)amino]-ethyl-phosphonic acid there was obtained (1R)-1-(L-phenylalanylamino)-ethylphosphonic acid of melting point ca 254° C (decomposition); $[\alpha]_D^{20} = -22.3°$ (c = 0.5% in water).

EXAMPLE 40 a. Preparation of the starting material

In a manner analogous to that given in Example 7 (a) but with ion-exchange in methanol/water, from the N-hydroxysuccinimide ester of N-benzyloxycarbonyl-L-phenylalanine there was obtained the benzylamine salt of [(N-benzyloxycarbonyl-L-phenylalanyl-L-alanyl)amino]-methylphosphonic acid of melting point 233°–234° C (decomposition); $[\alpha]_D^{20} = -2.7°$ (c = 0.6% in glacial acetic acid).

b. The process

In a manner analogous to that given in Example 7 (b), from the benzylamine salt of [(N-benzyloxycarbonyl-L-phenylalanyl-L-alanyl)amino]-methylphosphonic acid there was obtained (L-phenylalanyl-L-alanylamino)-methylphosphonic acid of melting point 262°–264° C (decomposition); $[\alpha]_D^{20} = -9.6°$ (c = 0.5% in water).

EXAMPLE 41 a. Preparation of the starting material

In a manner analogous to that given in Example 7 (a) but with ion-exchange in methanol, from the N-hydroxysuccinimide ester of N-benzyloxycarbonyl-L-phenylalanine and (L-phenylalanylamino)-methylphosphonic acid there was obtained [(N-benzyloxycarbonyl-L-phenylalanyl-L-phenylalanyl)amino]-methylphosphonic acid of melting point 200°-210° C (decomposition).

b. The process

In a manner analogous to that given in Example 7 (b), from [(N-benzyloxycarbonyl-L-phenylalanyl-L-phenylalanyl)-amino]-methylphosphonic acid there was obtained (L-phenylalanyl-L-phenylalanylamino)-methylphosphonic acid of melting point 275°–277° C (decomposition); $[\alpha]_{578}^{20} = +10.4°$ (c = 0.2% in 1-N sodium hydroxide).

EXAMPLE 42 a. Preparation of the starting material

In a manner analogous to that given in Example 7 (a) but with ion-exchange in methanol/water, from the N-hydroxysuccinimide ester of N-benzyloxycarbonyl-L-alanine and (L-phenylalanylamino)-methylphosphonic acid there was obtained the benzylamine salt of [(N-benzyloxycarbonyl-L-alanyl-L-phenylalanyl)amino]-methylphosphonic acid of melting point 232°–234° C (decomposition); $[\alpha]_D^{20} = +3.0°$ (c = 0.6% in glacial acetic acid).

b. The process

In a manner analogous to that given in Example 7 (b), from the benzylamine salt of [(N-benzyloxycarbonyl-L-alanyl-L-phenylalanyl)amino]-methylphosphonic acid there was obtained (L-alanyl-L-phenylalanylamino)-methylphosphonic acid of melting point 278°–280° C (decomposition); $[\alpha]_D^{20} = +8.6°$ (c = 0.54% in 1-N sodium hydroxide).

EXAMPLE 43 a. Preparation of the starting material:

In a manner analogous to that given in Example 34 (a) but with ion-exchange in ethanol/water, from the N-hydroxysuccinimide ester of N-benzyloxycarbonyl-L-phenylalanine and (1R)-1-(L-alanylamino)-ethylphosphonic acid there was obtained (1R)-1-[(N-benzyloxycarbonyl-L-phenylalanyl-L-alanyl)amino]-ethylphosphonic acid of melting point 220°–221° C (decomposition); $[\alpha]_D^{20}$ −27.1° (c = 1.1% in glacial acetic acid).

b. The process

In a manner analogous to that given in Example 35 (b), from (1R)-1-[(N-benzyloxycarbonyl-L-phenylalanyl-L-alanyl)-amino]-ethylphosphonic acid there was obtained (1R)-1-(L-phenylalanyl-L-alanylamino)-ethylphosphonic acid of melting point 285°–287° C (decomposition); $[\alpha]_D^{20} = -28.1°$ (c = 0.5% in 1-N sodium hydroxide).

EXAMPLE 44 a. Preparation of the starting material:

In a manner analogous to that given in Example 2 (a) but using petroleum ether instead of toluene and methanol/water for the ion-exchange, from N-benzyloxycarbonyl-L-valine and (1R)-1-(L-alanylamino)-ethylphosphonic acid there was obtained the benzylamine salt of (1R)-1-[(N-benzyloxycarbonyl-L-valyl-L-alanyl)amino]-ethylphosphonic acid of melting point 250°–251° C (decomposition); $[\alpha]_D^{20} = -47.2°$ (c = 1% in glacial acetic acid).

b. The process

In a manner analogous to that given in Example 35 (b), from the benzylamine salt of (1R)-1-[(N-benzyloxycarbonyl-L-valyl-L-alanyl)amino]-ethylphosphonic acid there was obtained (1R)-1-(L-valyl-L-alanylamino)-ethylphosphonic acid of melting point 263°–265° C (decomposition); $[\alpha]_D^{20} = -44.6°$ (c = 0.5% in water).

EXAMPLE 45 a. Preparation of the starting material

In a manner analogous to that given in Example 35 (a), from the N-hydroxysuccinimide ester of N-benzyloxycarbonyl-L-alanine and (1R)-1-(L-alanyl-L-alanylamino)-ethylphosphonic acid there was obtained (1R)-1-[(N-benzyloxycarbonyl-L-alanyl-L-alanyl-L-alanyl)amino]-ethylphosphonic acid of melting point 255°–257° C (decomposition); $[\alpha]_D^{20} = -62.0°$ (c = 0.4% in glacial acetic acid).

b. The process

In a manner analogous to that given in Example 35 (b), from (1R)-1-[(N-benzyloxycarbonyl-L-alanyl-L-alanyl-L-alanyl)-amino]-ethylphosphonic acid there was obtained (1R)-1-(L-alany-L-alanyl-L-alanylamino)-ethylphosphonic acid of melting point 312°–313° C (decomposition); $[\alpha]_D^{20} = -101°$ (c = 0.53% in 1-N sodium hydroxide).

EXAMPLE 46 a. Preparation of the starting material:

In a manner analogous to that given in Example 45 (a), from the N-hydroxysuccinimide ester of N-benzyloxycarbonyl-L-alanine and (1R)-1-(L-alanyl-L-alanyl-L-alanylamino)-ethylphosphonic acid there was obtained, on acidification and without recourse to ion-exchange, the free acid. The latter was filtered off, washed with water and acetone and dried to give the pure free acid, namely (1R)-1-[(N-benzyloxycarbonyl-L-alanyl-L-alanyl-L-alanyl-L-alanyl)amino]-ethylphosphonic acid of melting point 270°–275° C (decomposition); $[\alpha]_D^{20} = -71.7°$ (c = 0.54% in 1-N sodium hydroxide).

b. The process:

In a manner analogous to that given in Example 45 (b), from (1R)-1-[(N-benzyloxycarbonyl-L-alanyl-L-alanyl-L-alanyl-L-alanyl)amino]-ethylphosphonic acid there was obtained (1R)-1-(L-alanyl-L-alanyl-L-alanyl-L-alanylamino)-ethylphosphonic acid of melting point 317°–319° C (decomposition); $[\alpha]_D^{20} = -114°$ (c = 0.51% in 1-N sodium hydroxide).

EXAMPLE 47 a. Preparation of the starting material

In a manner analogous to that given in Example 11 (a), from the N-hydroxysuccinimide ester of N-benzyloxycarbonyl-L-alanine and (1R,S)-1-amino-2-phenyl-ethylphosphonic acid there was obtained a diastereomeric mixture of (1R,S)-1-[(N-benzyloxycarbonyl-L-alanyl)amino]-2-phenyl-ethylphosphonic acid. The mixture was separated by conversion to the benzylamine salts and crystallization from water. There was obtained the benzylamine salt of (1R)-1-[(N-benzyloxycarbonyl-L-alanyl)-amino]-2-phenyl-ethylphosphonic acid of melting point 223°–226° C (decomposition); $[\alpha]_D^{20} = -46.5°$ (c = 0.53% in glacial acetic acid).

b. The process

In a manner analogous to that given in Example 1 (b) but with ion-exchange in methanol, from the benzylamine salt of (1R)-1-[(N-benzyloxycarbonyl-L-alanyl)amino]-ethylphosphonic acid there was obtained (1R)-1-(L-alanylamino)-2-phenylethylphosphonic acid of melting point 250°–260° C (decomposition); $[\alpha]_D^{20} = -40.3°$ (c = 0.21% in water).

The following Example illustrates a typical pharmaceutical preparation containing a peptide derivative provided by the present invention:

EXAMPLE A

A 1000 ml injection solution was manufactured which contained the following ingredients:

|  | Per 1000 ml |
|---|---|
| (1R)-1-(L-Alanylamino)-ethylphosphonic acid | 100.0 g |
| Chlorocresol | 1.0 g |
| Acetic acid (glacial) | 1.2 g |
| Sodium hydroxide solution (0.1-N) q.s. | pH 4.5 |
| Water for injections | ad 1000 ml |

The (1R)-1-(L-alanylamino)-ethylphosphonic acid is dissolved in 500 ml of water for injections. The chlorocresol was dissolved in 200 ml of water for injections and added to the first solution. The acetic acid was then added while stirring. A 0.1-N solution of sodium hydroxide in water for injections was added while stirring until a pH value of 4.5 was given. The solution was then made up to 1000 ml with water for injections, filtered through a sterile 0.22 micron membrane filter and filled out into ampoules. The ampoules were sealed and then sterilised by autoclaving at 121° C for 20 minutes.

We claim:

1. A compound of the formula

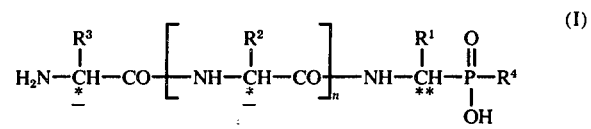

wherein $R^1$ is hydrogen, lower alkyl, lower cycloalkyl, lower alkyl substituted with lower cycloalkyl or aryl, said groups other than hydrogen being optionally substituted by one or more of amino, hydroxy, thio, methylthio, carboxy or guanidino so as to form the side chain of a naturally occurring L alpha-amino acid; $R^2$ and $R^3$ each is the side chain of an alpha-amino acid of the type normally found in proteins with the proviso that $R^3$ cannot be hydrogen when n is zero and $R^1$ is hydrogen or phenyl; $R^4$ is hydroxy or methyl; n is zero, 1, 2 or 3; the single asterisks denote that the configuration at the carbon atom so-marked is L; and the double asterisk denotes that when $R^1$ is other than hydrogen, the configuration at the carbon atom so-marked is R. and pharmaceutically acceptable salts thereof, 2. The compounds of claim 1 of the formula

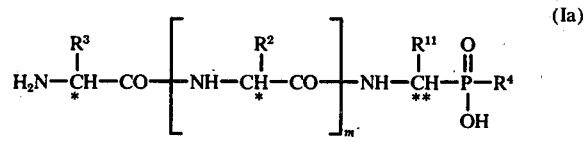

wherein $R^{11}$ is hydrogen, lower alkyl, aryl or aryl-(lower alkyl); $R^2$ and $R^3$ each is the side chain of an alpha-amino acid of the type normally found in proteins with the proviso that $R^3$ cannot be hydrogen when m is zero and $R^{11}$ is hydrogen; $R^4$ is hydroxy or methyl; m is zero, 1 or 2; the single asterisks denote that the configuration at the carbon atom so marked is L; and the double asterisk denotes that when $R^{11}$ is other than hydrogen, the configuration at the carbon atom so marked is R, and pharmaceutically acceptable salts thereof.

3. The compound of claim 2 wherein $R^2$ and $R^3$ each is hydrogen, methyl, isopropyl, isobutyl, benzyl, 4-aminobutyl or 2-pyrrolidinyl, $R^{11}$ is hydrogen or methyl, $R^4$ is hydroxy and m is zero or 1 and pharmaceutically acceptable salts thereof.

4. The compound of claim 3 which is (1R)-1-(L-alanylamino)-ethylphosphonic acid.

5. The compound of claim 3 which is (L-alanylamino)-methylphosphonic acid.

6. A compound of claim 1 selected from the group of ethyl phosphonic acids consisting of (1R)-1-glycylamino-ethylphosphonic acid, (1R)-1-(L- alanylamino)-benzylphosphonic acid, (1R)-1-(L-prolylamino)-ethylphosphonic acid, (1R)-1-(L-lysylamino)-ethylphosphonic acid, (1R)-1-(L-leucylamino)-ethylphosphonic acid, (1R), -1-(L-alanylamino)-2-phenyl-ethylphosphonic acid, (1R)-1-(L-phenylalanylamino)-ethylphosphonic acid, (1R)-1-(L-valylamino)-ethylphosphonic acid, (1R)-1-(L-alanyl-L-alanylamino)-ethyl-phosphonic acid, (1R)-1-(glycyl-L-alanylamino)-ethylphosphonic acid, (1R)-1-(L-valyl-L-alanylamino)-ethylphosphonic acid, (1R)-1-(L-phenylalanyl-L-alanylamino)-ethylphosphonic acid, (1R)-1-(L-prolyl-L-alanylamino)-ethylphosphonic acid, (1R)-1-L-alanyl-L-alanyl-L-alanylamino)-ethylphosphonic acid, (1R)-1-(glycyl-L-alanyl-L-alanylamino)-ethylphosphonic acid, (1R)-1-(glycyl-glycyl-L-alanylamino)-ethylphosphonic acid, and (1R)-1(L-alanyl-L-alanyl-1-alanyl-L-alanylamino)-ethylphosphonic acid.

7. A compound of claim 1 selected from the group of methylphosphonic acids consisting of (L-valylamino)-methylphosphonic acid, (L-leucylamino)methylphosphonic acid (L-lysylamino)-methylphosphonic acid, (L-phenylalanylamino)-methylphosphonic acid, (L-alanyl-L-alanylamino)-methylphosphonic acid, (L-leucyl-L-alanylamino)-methylphosphonic acid, (L-alanyl-L-leucylamino)-methylphosphonic acid, (L-alanyl-L-phenylalanylamino)-methylphosphonic acid, (L-phenylalanyl-L-alanylamino)-methylphosphonic acid, and (L-alanyl L-alanyl-L-alanylamino)-methylphosphonic acid.

8. The compound of claim 1 which is -methylphosphinic acid.

9. A compound of the formula

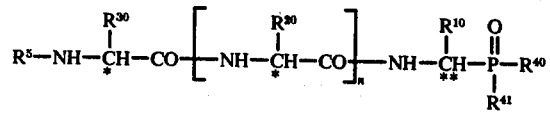

(II)

wherein $R^{10}$ is hydrogen, lower alkyl, lower cycloalkyl, aryl or lower alkyl substituted with lower cycloalkyl or aryl, said groups other than hydrogen being optionally substituted by one or more of amino, hydroxy, thio, methylthio, carboxy or guanidino so as to form the side chain of a naturally occurring L alpha-amino acid; $R^{20}$ and $R^{30}$ each is the side chain of an alpha-amino acid of the type normally found in proteins with the proviso that $R^{30}$ cannot be hydrogen when $n$ is zero and $R^{10}$ is hydrogen or phenyl; except that any amino group or amino groups present may be in protected form utilizing a conventional amino protecting group and any other functional group which may be present is in protected form where required, $R^{40}$ is methyl or $R^{41}$, $R^{41}$ is hydroxy or lower alkoxy, $R^5$ is hydrogen or a conventional amino protecting group, $n$ is zero, 1, 2 or 3; the single asterisks denote that the configuration at the carbon atom so-marked is L; and the double asterisk denotes that, when $R^1$ is other than hydrogen, the configuration at the carbon atom so-marked is R.

10. A compound of the formula

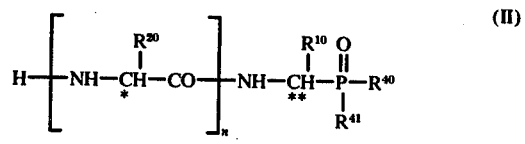

(II)

wherein $R^{10}$ is hydrogen, lower alkyl, lower cycloalkyl, aryl or lower alkyl substituted with lower cycloalkyl or aryl, said groups other than hydrogen being optionally substituted by one or more of amino, hydroxy, thio, methylthio, carboxy or guanidino so as to form the side chain of a naturally occurring L alpha-amino acid; $R^{20}$ is the side chain of an alpha-amino group or amino groups present may be in protected form utilizing a conventional amino protecting group and any other functional group which may be present is in protected form where required, $R^{40}$ is methyl or $R^{41}$, $R^{41}$ is hydroxy or lower alkoxy, $R^5$ is hydrogen or a conventional amino protecting group, $n$ is zero, 1, 2 or 3; the single asterisks denote that the configuration at the carbon atom so-marked is L; and the double asterisk denotes that, when $R^1$ is other than hydrogen, the configuration at the carbon atom so-marked is R.

* * * * *

UNITED STATES PATENT AND TRADEMARK OFFICE
CERTIFICATE OF CORRECTION

PATENT NO. : 4,016,148

DATED : April 5, 1977

INVENTOR(S) : Frank Ratcliffe Atherton, Michael John Hall, Cedric Herbert Hassall, Peter Stuart Ringrose and Robert Wilson Lambert It is certified that error appears in the above-identified patent and that said Letters Patent are hereby corrected as shown below:

Claim 1, column 28, line 22, after "kyl," should be: aryl or

Claim 1, column 28, line 35, "R." should be: R,

Claim 1, column 28, line 36, "thereof," should be: thereof.

Claim 6, column 29, line 17, "alanyl-1-alanyl" should be —alanyl-L-alanyl—

Claim 7, column 29, line 21, "(L-leucylamino)methylphos-" should be (L-leucylamino)-methylphos- Claim 8, column 29, line 31, "is -methylphos-" should be is [(L-alanylamino)methyl] -methylphos- Signed and Sealed this Twenty-fifth Day of October 1977

[SEAL]

Attest:

RUTH C. MASON
*Attesting Officer*

LUTRELLE F. PARKER
*Acting Commissioner of Patents and Trademarks*